United States Patent
Durando (12) 
(10) Patent No.: US 9,314,571 B1
(45) Date of Patent: Apr. 19, 2016

(54) DRUG DELIVERY SYSTEM

(71) Applicant: mPhase Technologies, Inc., Little Falls, NJ (US)

(72) Inventor: Ronald Durando, Little Falls, NJ (US)

(73) Assignee: mPhase Technologies, Inc., Little Falls, NJ (US)

( * ) Notice: Subject to any disclaimer, the term of this patent is extended or adjusted under 35 U.S.C. 154(b) by 276 days.

(21) Appl. No.: 13/763,893

(22) Filed: Feb. 11, 2013

Related U.S. Application Data (60) Provisional application No. 61/597,276, filed on Feb. 10, 2012.

(51) Int. Cl.
| | |
|---|---|
| *A61F 7/12* | (2006.01) |
| *A61M 5/00* | (2006.01) |
| *A61M 5/168* | (2006.01) |
| *A61M 5/44* | (2006.01) |

(52) U.S. Cl.
CPC *A61M 5/168* (2013.01); *A61M 5/44* (2013.01)

(58) Field of Classification Search
CPC . A61K 9/0097; A61K 9/0009; A61K 9/7023; A61K 9/703; A61K 9/7084; A61K 9/7092; A61K 9/00; A61K 9/0012; A61K 9/70; A61K 9/7007; A61M 2205/0244; A61M 15/0031; A61M 15/0045; A61M 15/005; A61M 37/00; A61M 5/1407; A61M 15/0048; A61M 2037/0007; A61M 31/002; A61M 37/0092; A61N 1/325; B81B 2201/058
USPC ........................................................ 604/113

See application file for complete search history.

(56) References Cited

U.S. PATENT DOCUMENTS

| | | | |
|---|---|---|---|
| 5,169,383 A * | 12/1992 | Gyory et al. | 604/20 |
| 5,281,198 A * | 1/1994 | Haber et al. | 604/86 |
| 5,336,213 A * | 8/1994 | D'Angelo et al. | 604/890.1 |
| 5,797,898 A | 8/1998 | Santini, Jr. | |
| 6,656,162 B2 * | 12/2003 | Santini et al. | 604/191 |
| 6,953,455 B2 | 10/2005 | Cho | |
| 7,092,753 B2 | 8/2006 | Darvish | |
| 7,114,312 B2 | 10/2006 | Coppeta | |
| 2005/0077584 A1 | 4/2005 | Uhland | |
| 2006/0275138 A1 | 12/2006 | Sheng | |
| 2007/0036835 A1 | 2/2007 | Coppeta | |

* cited by examiner

*Primary Examiner* — Jason Flick
(74) *Attorney, Agent, or Firm* — Ohlandt, Greeley, Ruggiero & Perle, L.L.P.

(57) ABSTRACT

A drug delivery system for automatically dispensing a pre-set dosage of a drug agent or medication. The drug delivery system generally includes a housing including one or more reservoirs; each having a medical agent hermetically sealed therein. A membrane extends across each of the one or more reservoirs which is adapted to allow the medical agents to pass therethrough in response to external stimuli, such as physical puncturing, melting the membranes through use of heating elements or electrowetting in response to a voltage pulse. A wicking material extends across the membranes through which the medical agents are dispensed to a patient. Because the housing can be made flat, the overall dispensing device can be reduced in size, allowing the drug delivery device to be located and attached to broader areas of the patient's body for expanded medical applications and treatment.

20 Claims, 12 Drawing Sheets

DRUG DELIVERY SYSTEM

CROSS REFERENCE TO RELATED APPLICATIONS

I hereby claim benefit under Title 35, United States Code, Section 119(e) of U.S. provisional patent application Ser. No. 61/597,276 filed Feb. 10, 2012. The 61/597,276 application is hereby incorporated by reference into this application.

STATEMENT REGARDING FEDERALLY SPONSORED RESEARCH OR DEVELOPMENT

Not applicable to this application.

BACKGROUND OF THE INVENTION

1. Field of the Invention

The present invention relates generally to a non-pump enabled drug delivery device and more specifically it relates to a drug delivery system for automatically dispensing a pre-set dosage of a drug agent or medication.

2. Description of the Related Art

Any discussion of the related art throughout the specification should in no way be considered as an admission that such related art is widely known or forms part of common general knowledge in the field.

Many individuals in present times require routine application of various medication and drug agents. For example, individuals afflicted with diabetes require routine injections or applications of insulin to maintain proper blood sugar levels. Other individuals require routine application of medicated creams and the like to treat various skin conditions.

In the past, such individuals have been required to manually measure out the required amount of the medication prior to manually applying the medication, such as by applying to the skin or via injection. However, such methodology is highly susceptible to human error. Particularly in those individuals with impacted mental states, it can be burdensome and, in some cases dangerous, to manually select dosages and apply medication. Further, it is often cost-prohibitive to secure an outside health professional to manage these affairs on a day-to-day basis.

Because of the inherent problems with the related art, there is a need for a new and improved drug delivery system for automatically dispensing a pre-set dosage of a drug agent or medication.

BRIEF SUMMARY OF THE INVENTION

The invention generally relates to a drug delivery system which includes a housing including one or more reservoirs; each having a medical agent hermetically sealed therein. A membrane extends across each of the one or more reservoirs which is adapted to allow the medical agents to pass therethrough in response to external stimuli, such as physical puncturing, melting the membranes through use of heating elements or electrowetting in response to a voltage pulse. A wicking material extends across the membranes through which the medical agents are dispensed to a patient.

There has thus been outlined, rather broadly, some of the features of the invention in order that the detailed description thereof may be better understood, and in order that the present contribution to the art may be better appreciated. There are additional features of the invention that will be described hereinafter and that will form the subject matter of the claims appended hereto. In this respect, before explaining at least one embodiment of the invention in detail, it is to be understood that the invention is not limited in its application to the details of construction or to the arrangements of the components set forth in the following description or illustrated in the drawings. The invention is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein.

DETAILED DESCRIPTION OF THE INVENTION

A. Overview

Turning now descriptively to the drawings, in which similar reference characters denote similar elements throughout the several views, FIGS. 1 through 12 illustrate a drug delivery system 10, which comprises a housing 20 including one or more reservoirs 30, 34, 37; each having a medical agent 31a, 31b, 31c hermetically sealed therein. A single layer membrane 40, 43, 46 extends across each of the one or more reservoirs 30, 34, 37 which is adapted to allow the medical agents 31a, 31b, 31c to pass therethrough in response to external stimuli, such as physical puncturing, melting the membranes 40, 43, 46 through use of heating elements 41, 44, 47 or electrowetting in response to a voltage pulse. A single layer wicking material 50 extends across the membranes 40, 43, 46 through which the medical agents 31a, 31b, 13 31c are dispensed to a patient. The single layer wicking material 50 has a first side directly in contact with single layer membrane 40, 43, 46 and a second side for direct contact with skin of a patient.

B. Housing and Reservoir(s)

Figure 1:
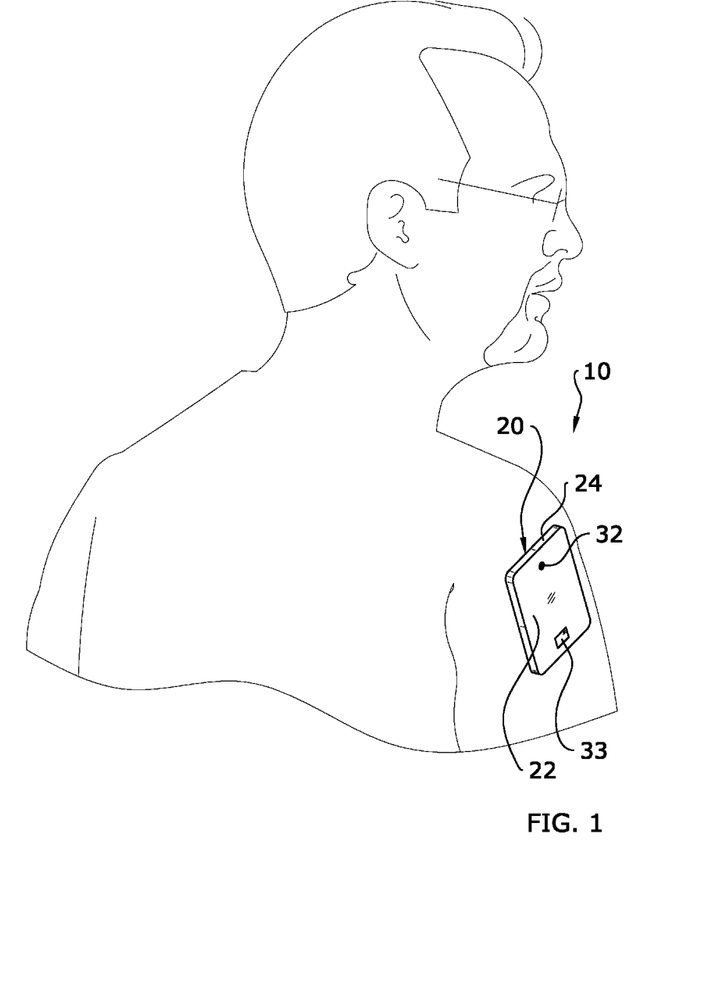
FIG. 1 is an upper perspective view of a first embodiment of the present invention in use.
Figure 2:
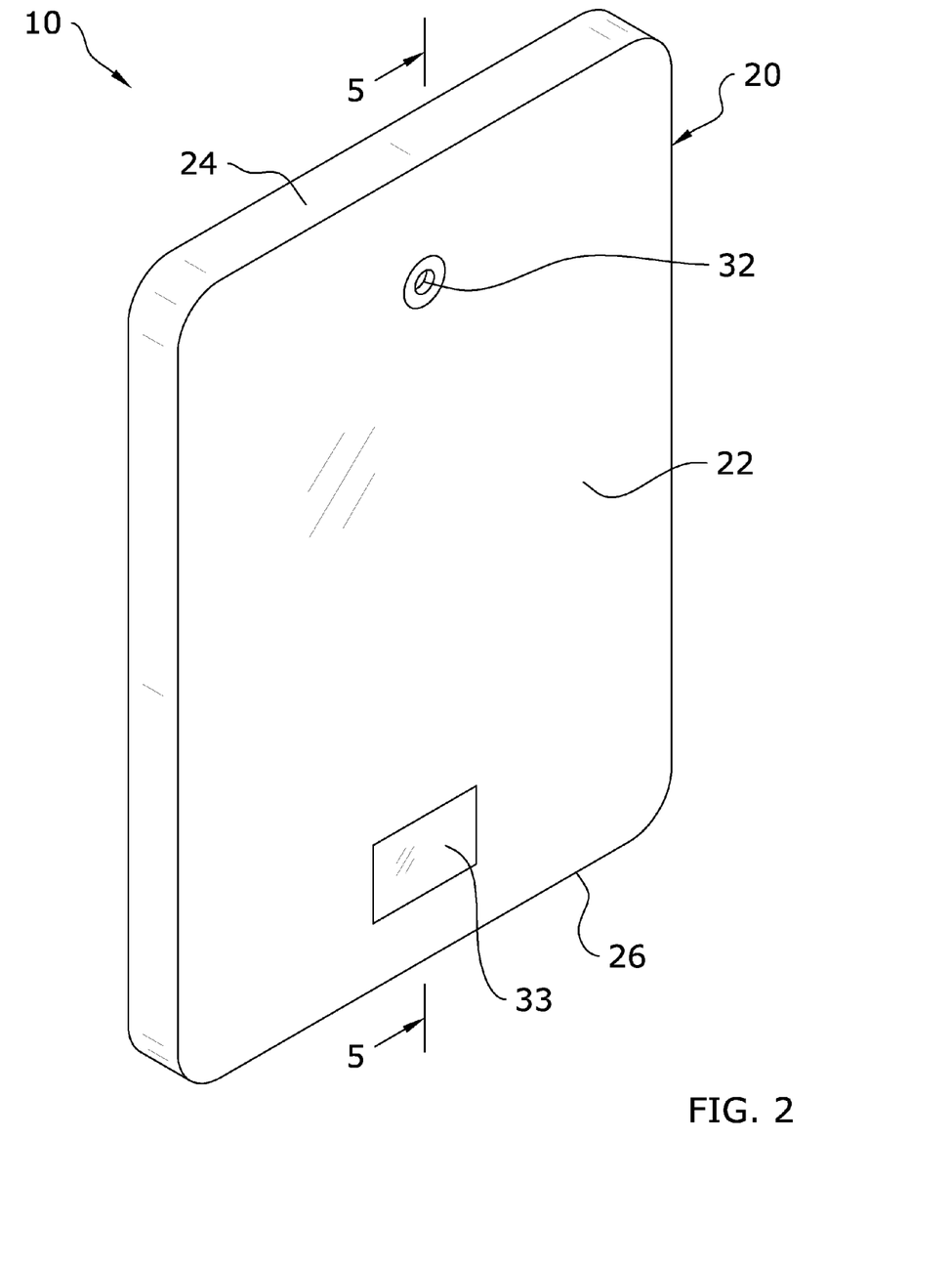
FIG. 2 is a rear upper perspective view of a first embodiment of the present invention.
Figure 3:
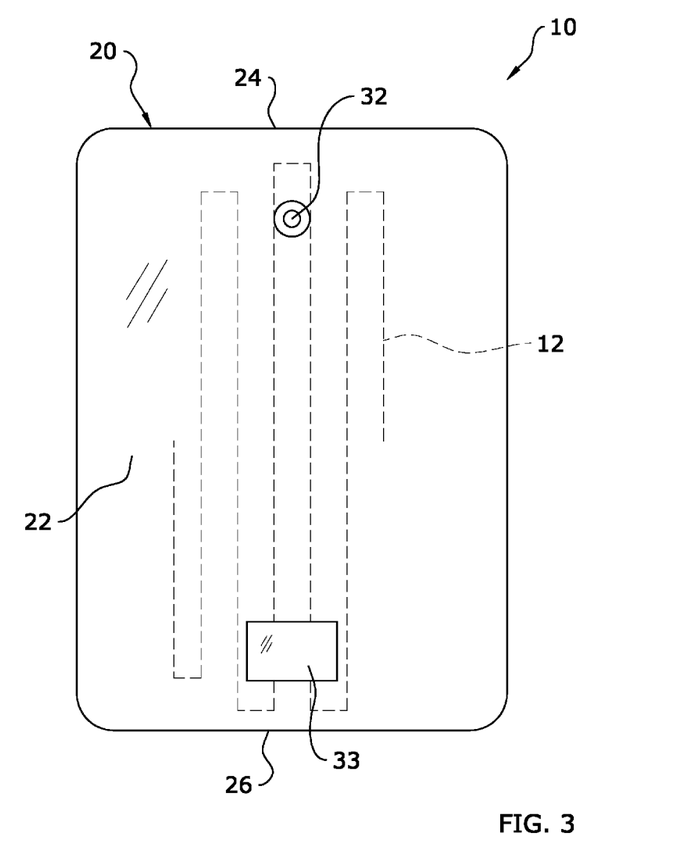
FIG. 3 is a rear view of a first embodiment of the present invention illustrating conduit pathing through the membrane.
Figure 4:
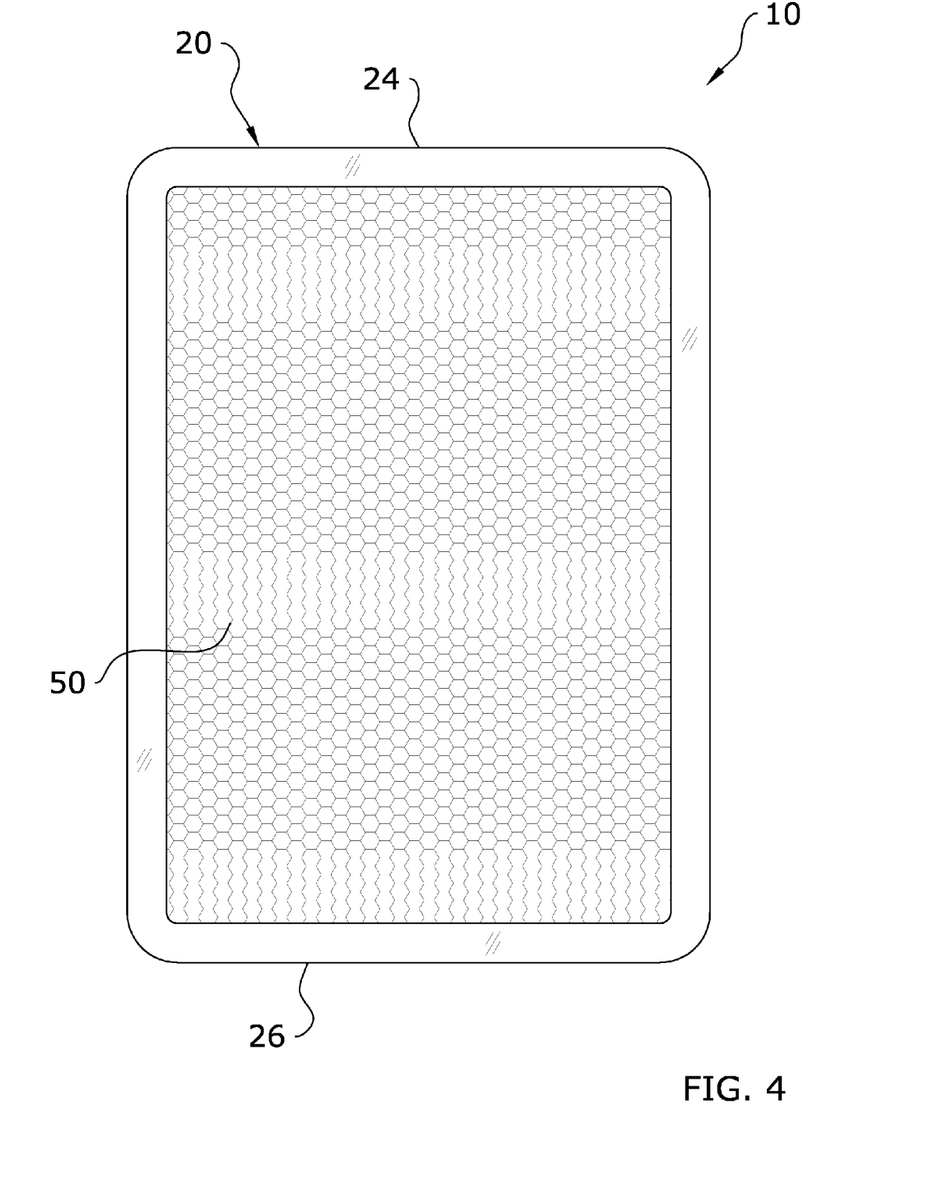
FIG. 4 is a frontal view of the present invention.
Figure 5:
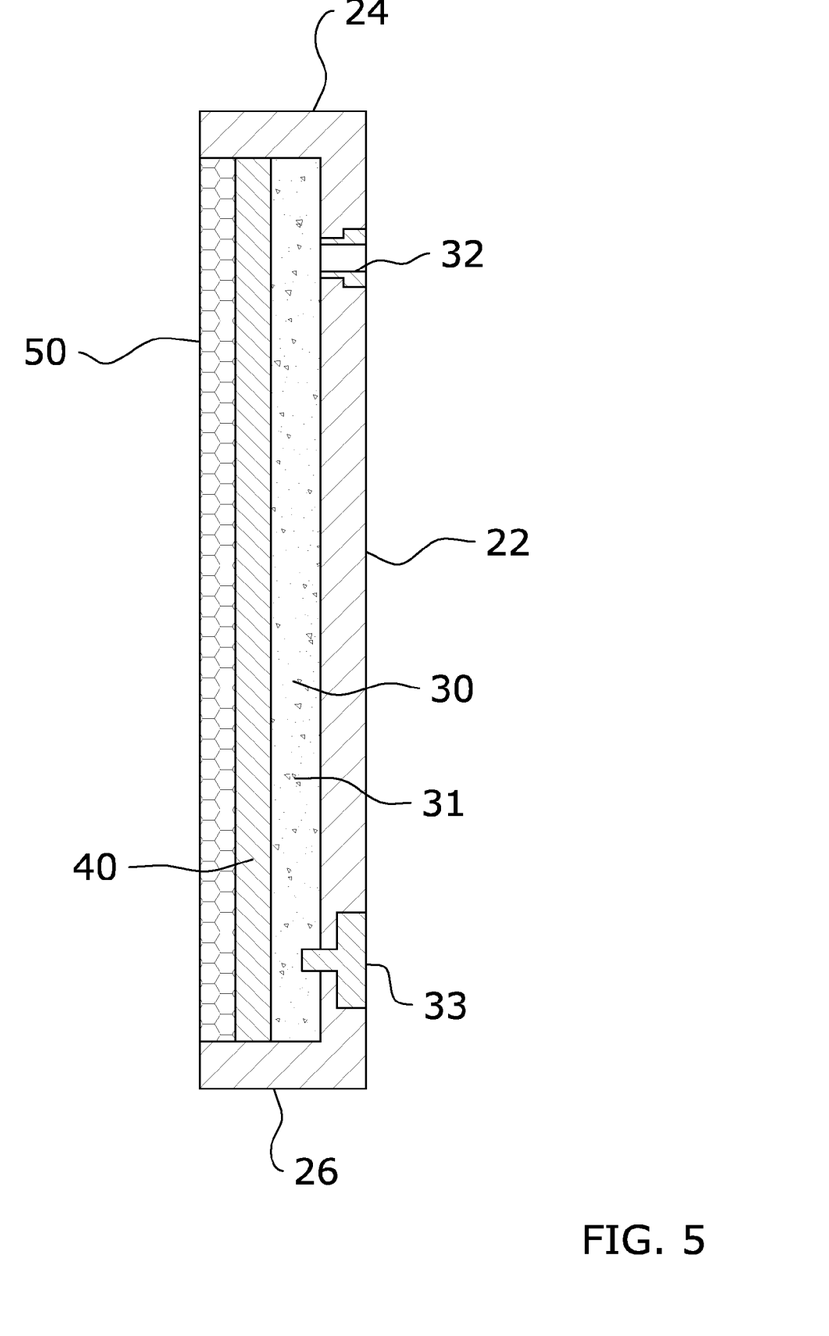
FIG. 5 is a side sectional view of a first embodiment of the present invention.
Figure 6:
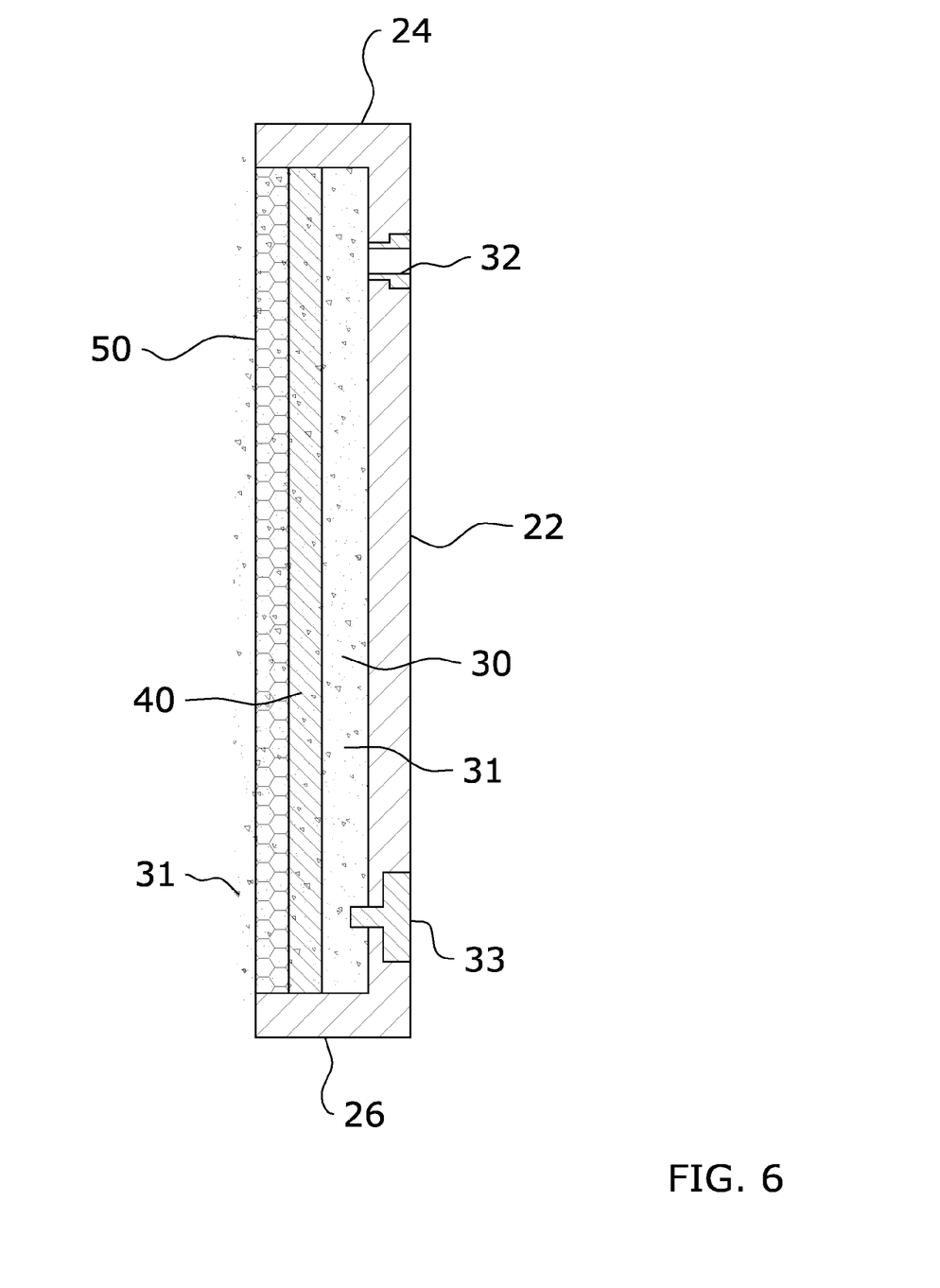
FIG. 6 is a side sectional view of a first embodiment of the present invention dispensing a medical agent.
Figure 7:
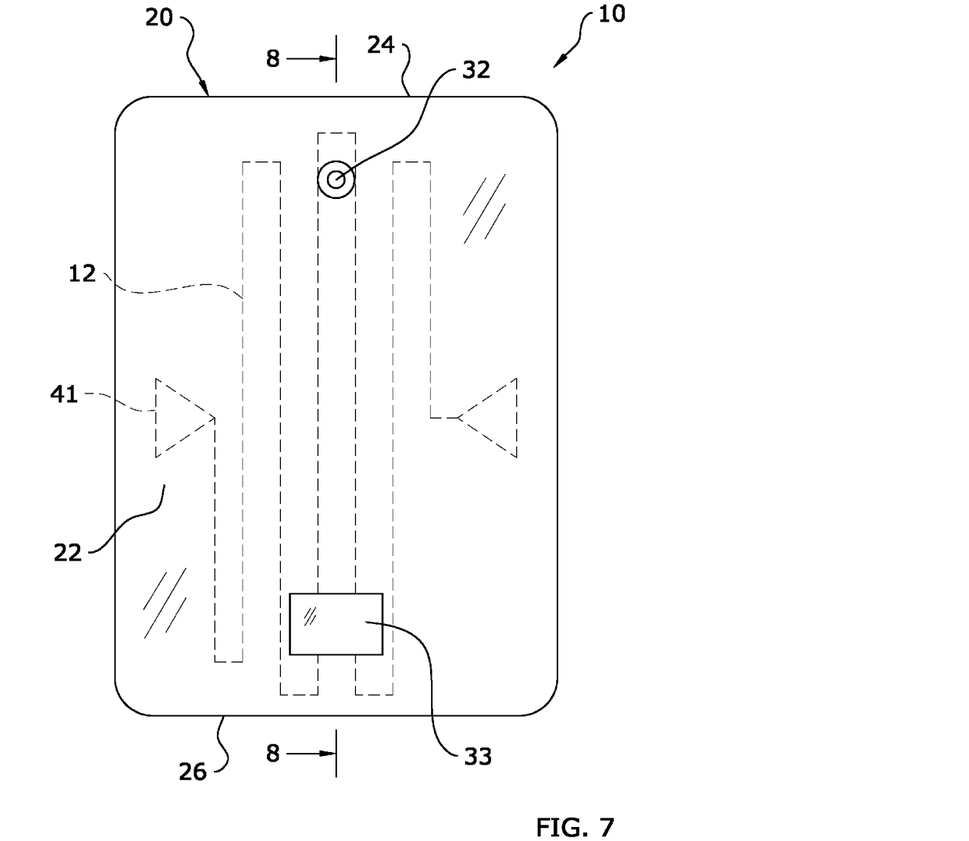
FIG. 7 is a rear view of a first embodiment of the present invention illustrating the usage of heating elements.
Figure 8:
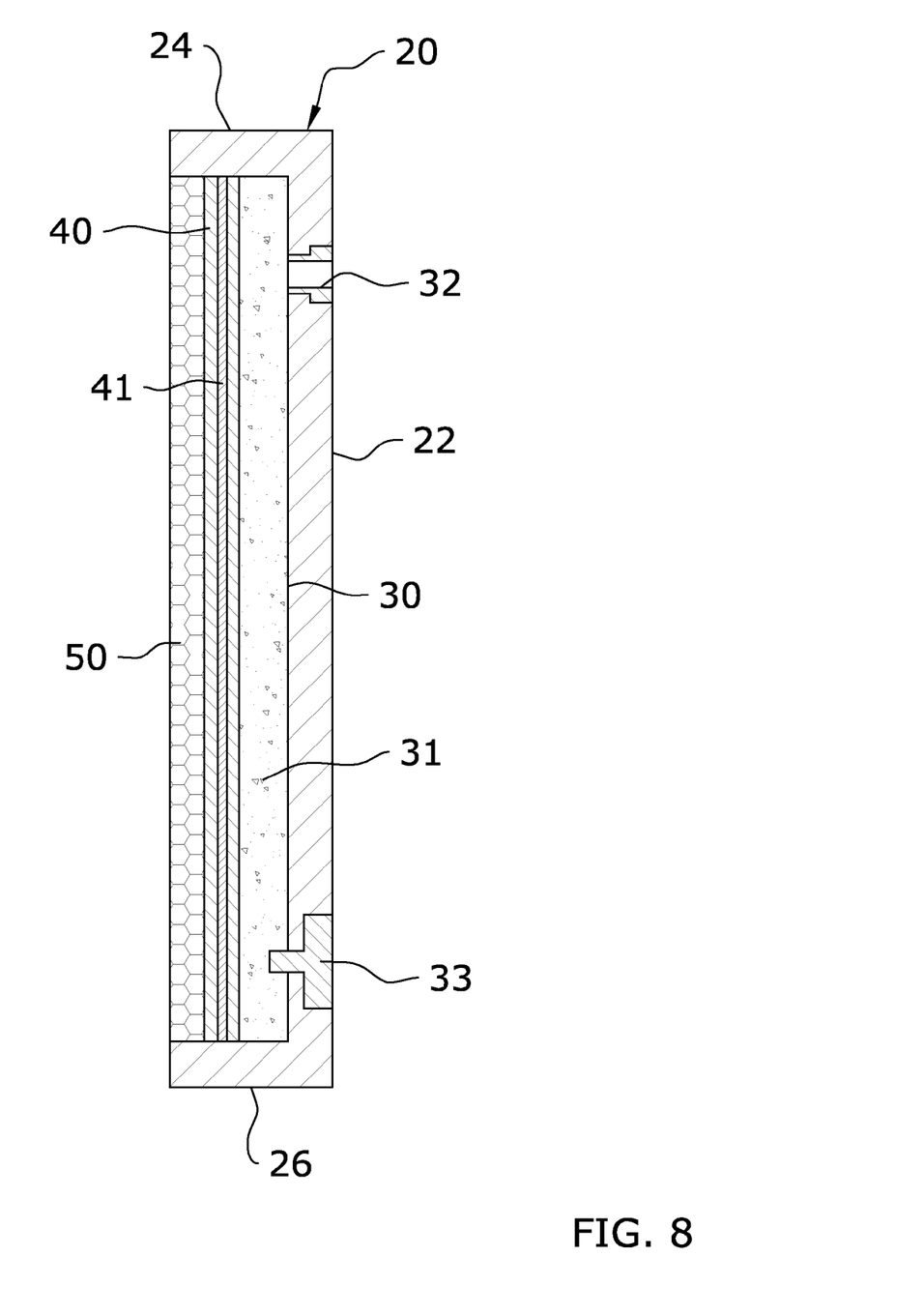
FIG. 8 is a side sectional view of a first embodiment of the present invention illustrating the usage of heating elements.
Figure 9:
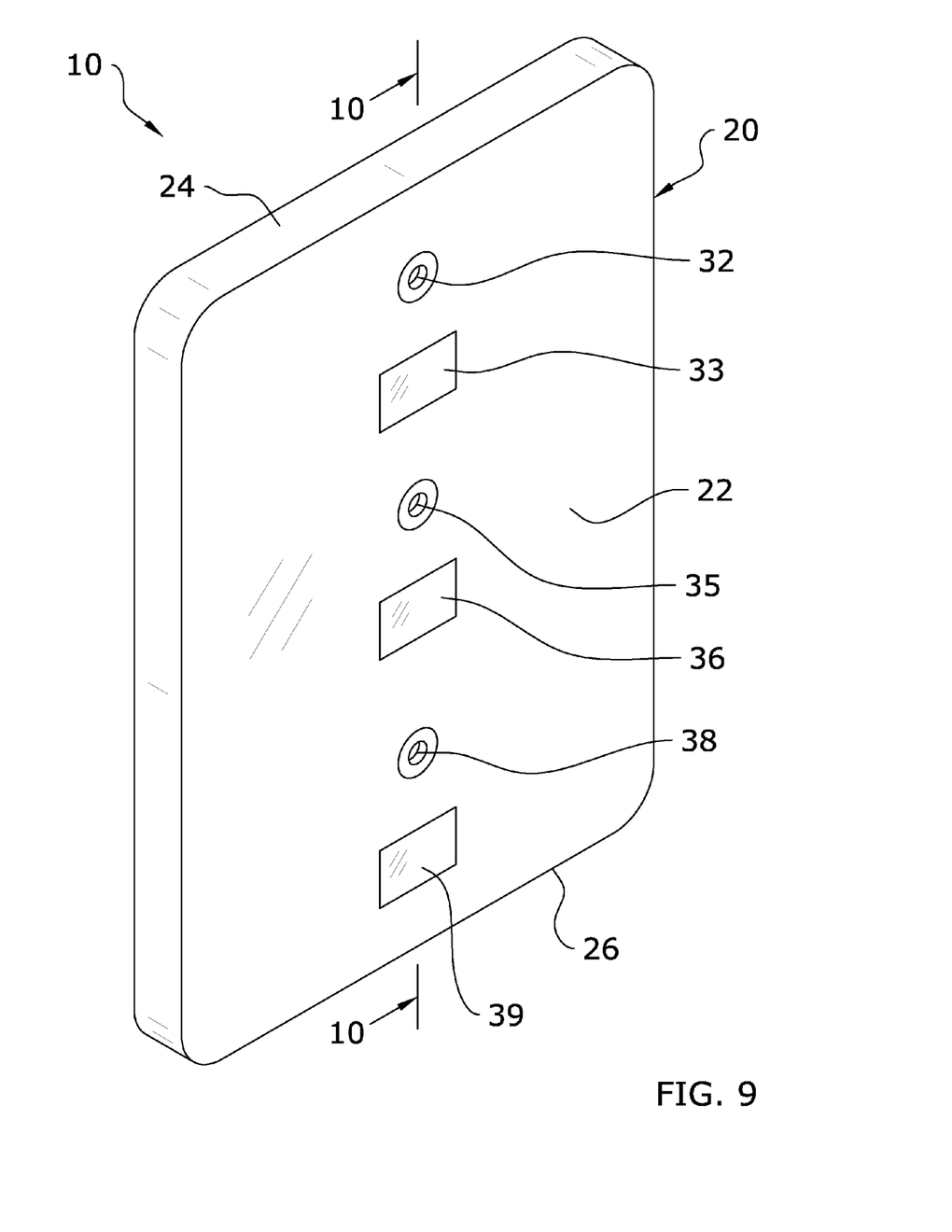
FIG. 9 is a rear upper perspective view of a second embodiment of the present invention.

As shown in FIG. 2, the present invention generally comprises a housing 20 which acts to store and dispense a predetermined amount of a medicated agent 31 in response to external stimulus. The shape, structure and configuration of the housing 20 may vary widely in different embodiments of the present invention. Thus, the rectangular housing 20 shown in the accompanying figures should not be construed as being limiting on the scope of the present invention as different shapes could be utilized for different embodiments.

In preferred embodiments as shown in the figures, the housing 20 will be comprised of an upper wall 22, a first sidewall 24 and a second sidewall 26. The walls 22, 24, 26 of the housing 20, in combination with the membrane 40, define a reservoir 30 adapted to store the medical agent 31 to be dispensed using the present invention. The walls 22, 24, 26 may be comprised of various materials which are capable of hermetically sealing the medical agent 31 within the reservoir 30 defined within the housing 20.

In the main embodiment shown in FIGS. 1-8, a single membrane 40 extends between the first sidewall 24 and second sidewall 26 to define the reservoir 30 in which the medical agent 31 is sealed. The volume of the reservoir 30, and thus the positioning of the membrane 40 on the sidewalls 24, 26, will vary depending on the application of the present invention. The specific construction of the membrane 40 will vary and is discussed in the following section of the present application.

The housing 20 will generally include a fill hole 32 and a triggering member 33 as shown in FIG. 2. The fill hole 32 is utilized to fill the reservoir 30 with the medical agent 31 to be applied with the present invention. The triggering member 33 is generally comprised of an electrode or other device which is utilized to provide the relevant stimulus to allow the medical agent 31 to pass through the membrane 40 and out through the wicking material 50 as discussed in more detail below. The positioning of the fill hole 32 and triggering member 33 may vary for different embodiments and thus should not be construed as being limited by the exemplary embodiments shown in the figures.

FIGS. 9-12 illustrate an alternate embodiment of the present invention which utilizes multiple reservoirs 30, 34, 37, each storing a separate medical agent 31a, 31b, 31c. While the figures only illustrate embodiments including one or three reservoirs 30, 34, 37, it is appreciated that varying numbers of reservoirs 30, 34, 37 may be included with the present invention in different embodiments.

The present invention should not be construed as being limited to these exemplary configurations, as some embodiments may include two reservoirs 30, 34 or four or more reservoirs 30, 34, 37 if needed. By utilizing multiple reservoirs 30, 34, 37, the present invention may accommodate storage and dispensing of different types of medical agents 31a, 31b, 31c within a single housing 20.

Figure 10:
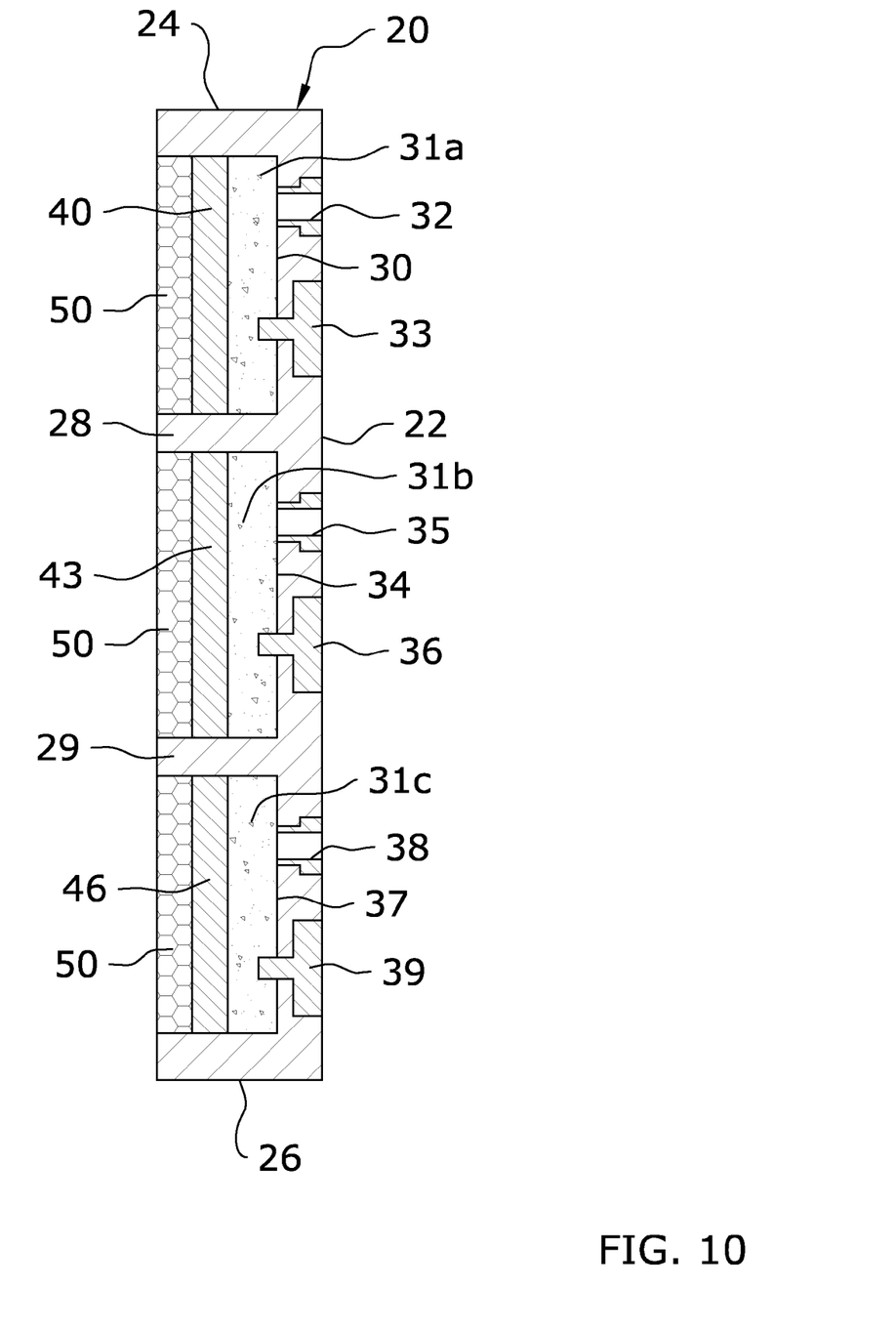
FIG. 10 is a side sectional view of a second embodiment of the present invention.
Figure 11:
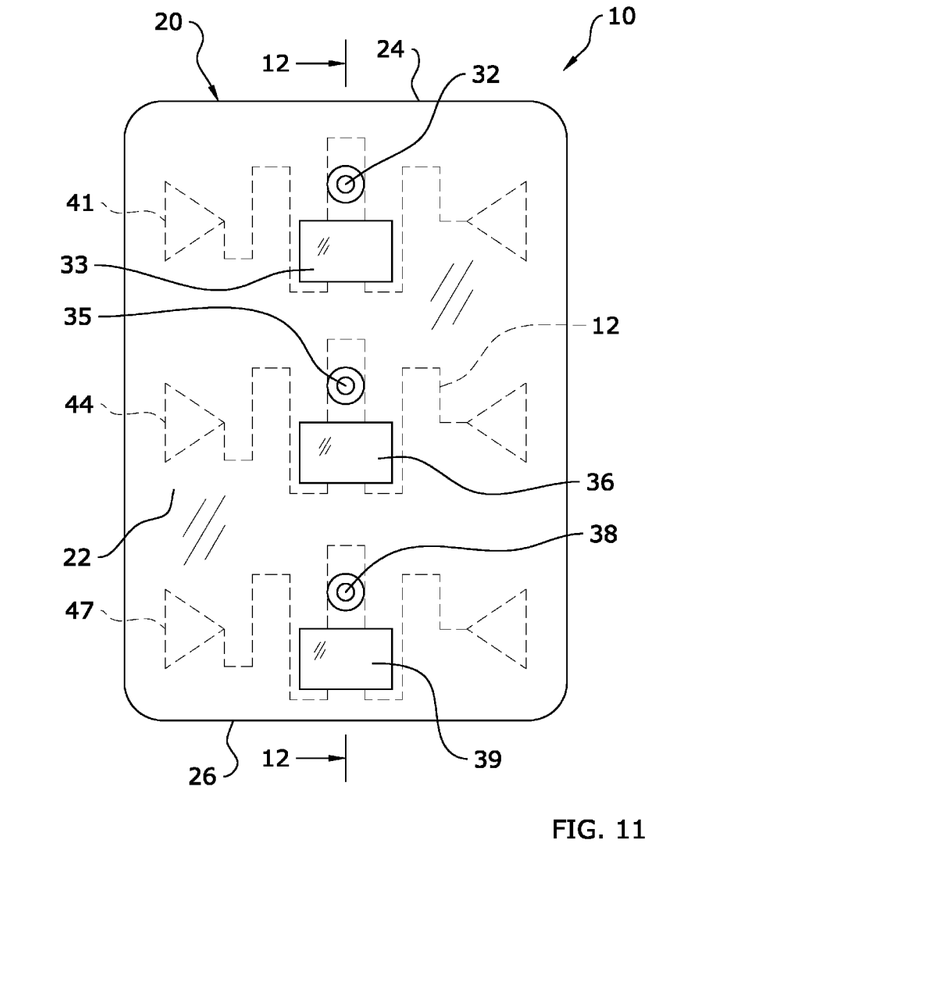
FIG. 11 is a rear view of a second embodiment of the present invention illustrating usage of heating elements.
Figure 12:
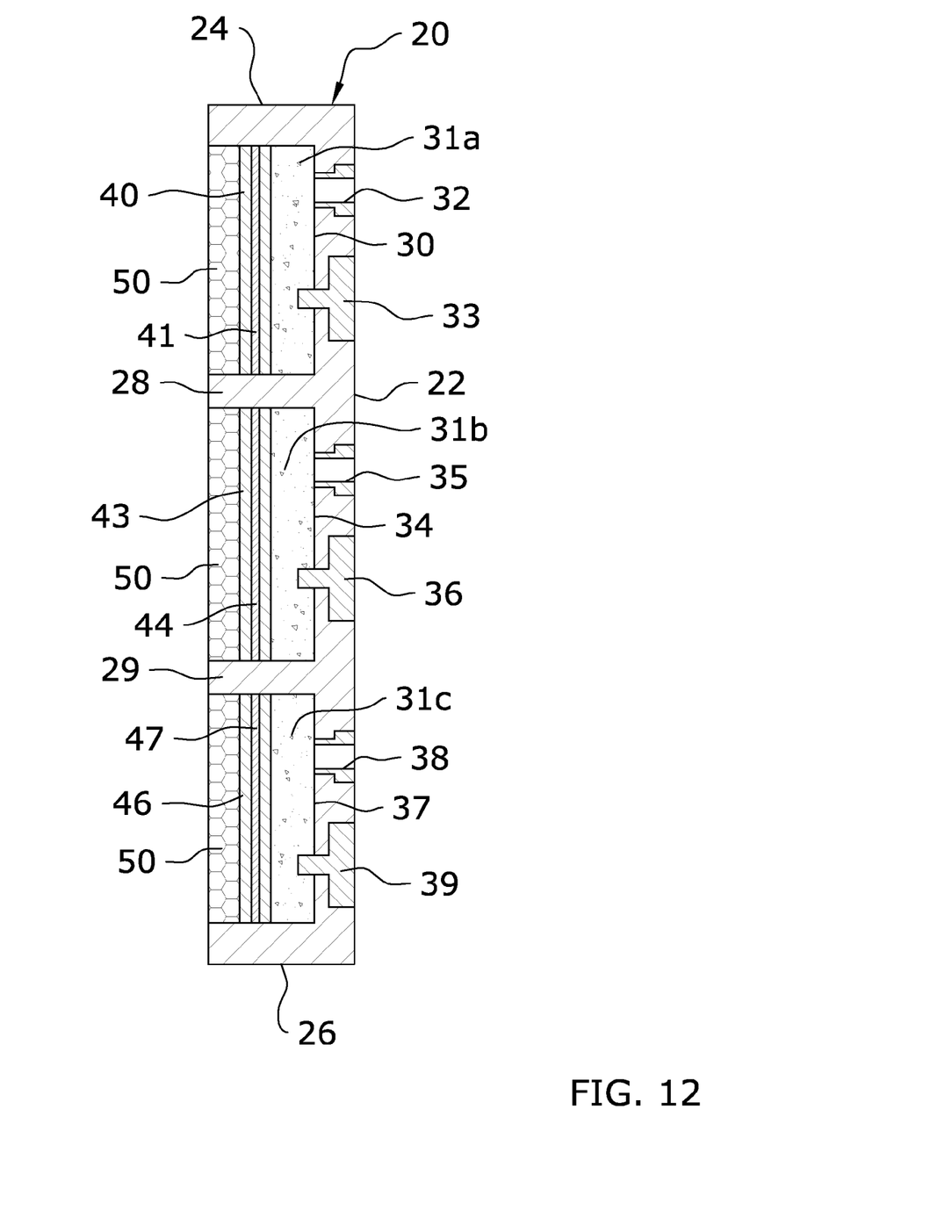
FIG. 12 is a side sectional view of a second embodiment of the present invention illustrating usage of heating elements.

In the alternate embodiment shown in FIGS. 9-12, the housing 20 includes a first divider wall 28 extending from a first point on the upper wall 22 and a second divider wall 29 extending from a second point on the upper wall 22 to define three discrete reservoirs 30, 34, 37 as shown in FIG. 10.

In such an embodiment, the housing 20 will include a first fill hole 32 and first triggering member 33 adjacent the first reservoir 30, a second fill hole 35 and second triggering member 36 adjacent the second reservoir 34 and a third fill hole 38 and third triggering member 39 adjacent the third reservoir 37. Thus, the different fill holes 32, 35, 38 may individually be utilized to fill each reservoir 30, 34, 37 with a different medical agent 31a, 31b, 31c. Similarly, the different triggering members 33, 36, 39 may be utilized to allow each medical agent 31a, 31b, 31c to pass through each of the three discrete membranes 40, 43, 46 in such an embodiment.

C. Membrane(s)

In the main embodiment shown in FIGS. 1-8, a single membrane 40 extends between the first sidewall 24 and second sidewall 26 of the housing 20. In the alternate embodiment shown in FIGS. 9-12, a first membrane 40 extends between the first sidewall 24 and first divider wall 28, a second membrane 42 extends between the first divider wall 28 and second divider wall 29 and a third membrane 46 extends between the second divider wall 29 and second sidewall 26 of the housing 20. Thus, in the alternate embodiment, each membrane 40, 43, 46 may be separately activated to dispense a different medical agent 31a, 31b, 31c.

The membranes 40, 43, 46 of the present invention may vary in different embodiments as to the type of external stimulus necessary to allow the medical agent 31 to pass therethrough. In one such embodiment, the membrane(s) 40, 43, 46 will be comprised of a porous, hydrophobic membrane 31 which is adapted to prevent the medical agent 31 to pass therethrough absent external stimulus.

When desired, a voltage pulse may be applied to the membrane(s) 40, 43, 46 through use of the triggering member(s) 33, 36, 39 which causes a transition of the surface properties of the membrane(s) 40, 43, 46 and medical agent(s) 31a, 31b, 31c. This transition results in the membrane(s) 40, 43, 46 losing their repelling properties and thus allowing the medical agent(s) 31a, 31b, 31c to pass through the porous regions of the membrane(s) 40, 43, 46 and into the wicking material 50 to be dispensed to the patient. In such an embodiment, conduit 12 is incorporated within the membrane(s) 40, 43, 46 through which the voltage pulse will be applied to the membrane(s) 40, 43, 46. The conduit 12 will be electrically connected to the trigger(s) 33, 36, 39 so that the voltage pulses may be transferred from the trigger(s) 33, 36, 39 to the membrane(s) 40, 43, 46 to electrically activate the same.

In an alternate embodiment, the membrane(s) 40, 43, 46 may be physically punctured such as by rupturing, puncturing or tearing the membrane(s) 40, 43, 46 using a physical trigger 33, 36, 39 such as a pin or similar structure. Alternatively, some embodiments may allow the housing 20 to be twisted to break the membrane(s) 40, 43, 46.

In yet another alternate embodiment as shown in FIGS. 7, 8, 11 and 12, one or more heating elements 41, 44, 47 may be utilized to melt the membrane(s) 40, 43, 46. In such an embodiment, a first heating element 41 will be incorporated into the first membrane 40, a second heating element 44 will be incorporated into the second membrane 43 and a third heating element 47 will be incorporated into the third membrane 46. The heating elements 41, 44, 47 will act to melt the membranes 40, 43, 46 in response to electrical or other stimulus initiated at the triggers 33, 36, 39 and transferred via conduit 12 to the heating elements 41, 44, 47. When the membranes 40, 43, 46 melt, the stored medical agents 31*a*, 31*b*, 31*c* will pass therethrough and into the wicking material 50.

D. Wicking Material

As shown throughout the figures, a wicking material 50 extends below the membrane(s) 40, 43, 46 of the present invention. The wicking material 50 may be comprised of any material capable of passing the medical agents 31*a*, 31*b*, 31*c* therethrough to be applied to the patient. In embodiments utilizing multiple reservoirs 30, 34, 37, three discrete wicking materials 50 will be utilized, each separated by the divider walls 28, 29, to prevent cross-contamination of the medical agents 31a, 31b, 31c when dispensed.

E. Operation of Preferred Embodiment

In use, the medical agents 31a, 31b, 31c are injected into the reservoirs 30, 34, 37 through the fill holes 32, 35, 38 on the upper wall 22 of the housing 20. When desired, the triggers 33, 36, 39 are activated to cause the medical agents 31a, 31b, 31c to pass through the membranes 40, 43, 46 and into the wicking material 50 to be dispensed to the patient. The wicking material 50 may be in direct contact with the patient's skin, if the medication can be absorbed through surface contact, or attached to some additional dispensing apparatus, such as a pump, if the medication needs to be injected into the patient's body.

It is appreciated that the step of triggering the membranes 40, 43, 46 may be accomplished through a wide range of means. For example, the triggering could be manually applied, such as by applying pressure to the triggers 33, 36, 39 in the case of a puncturing embodiment or applying a voltage thereto in the case of electrowetting membranes 40, 43, 46 or heating elements 41, 44, 47.

In other embodiments, the membranes 40, 43, 46 may be automatically triggered, such as through use of an external timer or controlling mechanism. The automatic triggering could be based on timing (i.e. set to trigger at specific times of the day) or may be adapted to trigger in response to detection of certain conditions (i.e. detection of blood sugar reaching a certain level).

Unless otherwise defined, all technical and scientific terms used herein have the same meaning as commonly understood by one of ordinary skill in the art to which this invention belongs. Although methods and materials similar to or equivalent to those described herein can be used in the practice or testing of the present invention, suitable methods and materials are described above. All publications, patent applications, patents, and other references mentioned herein are incorporated by reference in their entirety to the extent allowed by applicable law and regulations. In case of conflict, the present specification, including definitions, will control. The present invention may be embodied in other specific forms without departing from the spirit or essential attributes thereof, and it is therefore desired that the present embodiment be considered in all respects as illustrative and not restrictive. Any headings utilized within the description are for convenience only and have no legal or limiting effect.

The invention claimed is:

1. A drug delivery device, comprising:
a housing, said housing comprising an upper wall, a first sidewall and a second sidewall;
a single layer membrane extending between said first sidewall and said second sidewall to define a reservoir;
a medical agent stored within said reservoir; and
a single layer wicking material having a first side directly in contact with said membrane and a second side for direct contact with skin of a patient, wherein said membrane is adapted to allow said medical agent to pass therethrough and into said wicking material in response to an external stimulus.

2. The drug delivery device of claim 1, wherein said external stimulus is comprised of puncturing said membrane.

3. The drug delivery device of claim 1, wherein said external stimulus is comprised of an electrical current.

4. The drug delivery device of claim 1, further comprising at least one heating element embedded in said membrane.

5. The drug delivery device of claim 1, wherein said upper wall of said housing includes at least one fill hole.

6. The drug delivery device of claim 5, wherein said upper wall of said housing includes a triggering member.

7. The drug delivery device of claim 6, wherein said triggering member is electrically connected with a conduit, said conduit being embedded in said membrane.

8. The drug delivery device of claim 1, wherein said membrane is comprised of a porous, hydrophobic material.

9. The drug delivery device of claim 8, wherein said membrane is adapted to lose its hydrophobic properties in response to a voltage pulse.

10. A drug delivery device, comprising:
a housing, said housing comprising an upper wall, a first sidewall, a second sidewall, a first divider wall and a second divider wall;
a first, single membrane extending between said first sidewall and said first divider wall to define a first hermetically sealed reservoir;
a second, single membrane extending between said first divider wall and said second divider wall to define a second hermetically sealed reservoir;
a third, single membrane extending between said second divider wall and said second sidewall to define a third hermetically sealed reservoir;
a first medical agent stored within said first hermetically sealed reservoir;
a second medical agent stored within said second hermetically sealed reservoir;
a third medical agent stored within said third hermetically sealed reservoir;
a first single layer wicking material having a first side directly in contact with said first membrane and a second side for direct contact with skin of a patient;
a second single layer wicking material having a first side directly in contact with said second membrane and a second side for direct contact with skin of a patient; and
a third single layer wicking material having a first side directly in contact with said third membrane and a second side for direct contact with skin of a patient.

11. The drug delivery device of claim 10, wherein said first membrane is adapted to allow said first medical agent to pass therethrough and into said first wicking material in response to a first external stimulus.

12. The drug delivery device of claim 11, wherein said second membrane is adapted to allow said second medical agent to pass therethrough and into said second wicking material in response to a second external stimulus.

13. The drug delivery device of claim 12, wherein said third membrane is adapted to allow said third medical agent to pass therethrough and into said third wicking material in response to a third external stimulus.

14. The drug delivery device of claim 11, wherein said first external stimulus is comprised of puncturing said membrane.

15. The drug delivery device of claim 11, wherein said first external stimulus is comprised of an applied voltage pulse.

16. The drug delivery device of claim 11, wherein each of said first membrane, said second membrane and said third membrane includes embedded heating elements.

17. The drug delivery device of claim 16, wherein each of said first membrane, said second membrane and said third membrane is adapted to melt in response to the heating of said embedded heating elements.

18. The drug delivery device of claim 10, further comprising a first triggering member on said upper wall of said housing, said first triggering member being electrically connected with a first conduit embedded in said first membrane.

19. The drug delivery device of claim 18, further comprising a second triggering member on said upper wall of said housing, said second triggering member being electrically connected with a second conduit embedded in said second membrane.

20. The drug delivery device of claim 19, further comprising a third triggering member on said upper wall of said housing, said third triggering member being electrically connected with a third conduit embedded in said third membrane.

\* \* \* \* \*